United States Patent
Nachabe et al.

(10) Patent No.: US 8,812,080 B2
(45) Date of Patent: Aug. 19, 2014

(54) ALGORITHM FOR PHOTONIC NEEDLE CONSOLE

(75) Inventors: Rami Nachabe, Eindhoven (NL); Bernardus Hendrikus Wilhelmus Hendriks, Eindhoven (NL); Augustinus Laurentius Braun, Heeze (NL); Marjolein Van Der Voort, Eindhoven (NL); Adrien Desjardins, Eindhoven (NL); Drazenko Babic, Eindhoven (NL); Nenad Mihajlovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 170 days.

(21) Appl. No.: 13/376,702

(22) PCT Filed: Jun. 7, 2010

(86) PCT No.: PCT/IB2010/052514
§ 371 (c)(1),
(2), (4) Date: Dec. 7, 2011

(87) PCT Pub. No.: WO2010/143119
PCT Pub. Date: Dec. 16, 2010

(65) Prior Publication Data
US 2012/0088991 A1    Apr. 12, 2012

(30) Foreign Application Priority Data

Jun. 10, 2009   (EP) ..................................... 09162429

(51) Int. Cl.
*A61B 5/05*   (2006.01)

(52) U.S. Cl.
USPC ........................................... 600/424; 600/407

(58) Field of Classification Search
None
See application file for complete search history.

(56) References Cited

U.S. PATENT DOCUMENTS

| | | | |
|---|---|---|---|
| 5,460,182 A | 10/1995 | Goodman et al. | |
| 5,769,791 A | 6/1998 | Benaron et al. | |
| 7,860,583 B2 * | 12/2010 | Condurso et al. | 700/2 |
| 2003/0073895 A1 | 4/2003 | Nields et al. | |
| 2004/0039274 A1 * | 2/2004 | Benaron et al. | 600/342 |
| 2006/0241450 A1 * | 10/2006 | Da Silva et al. | 600/443 |
| 2008/0058794 A1 | 3/2008 | MacAdam et al. | |
| 2008/0188729 A1 | 8/2008 | Sato et al. | |

FOREIGN PATENT DOCUMENTS

| WO | WO0113796 | 3/2001 |
|---|---|---|
| WO | 2007083991 A1 | 7/2007 |

* cited by examiner

*Primary Examiner* — Unsu Jung
*Assistant Examiner* — Joel Lamprecht

(57) ABSTRACT

Needles are widely used in interventional radiology. Each medical application requires a specific needle type. The same holds for the photonic needles which analysis depends on the type of application the clinician aims for. Therefore, it is relevant to have the X-ray machine recognize the type of needle that is being used and to load the required software for the tissue analysis. It is therefore proposed to have a data link established between the imaging modality used for the acquisition of the patient anatomy (X-ray, CT, MR or US) and the system that processes optical data from the needle, so that the information from this imaging modality can be used to guide the processing. In a preferred embodiment the selection is made by reading out the code present in the disposable needle when it is connected to the console.

15 Claims, 7 Drawing Sheets

ALGORITHM FOR PHOTONIC NEEDLE CONSOLE

FIELD OF THE INVENTION

The present invention relates to the field of medical interventions and especially to the field of percutaneous needle-mediated interventions. In particular, the invention refers to a system for tissue inspection, including a needle device and a console, as well as to a software program adapted to be executed on the console.

TECHNOLOGICAL BACKGROUND

Percutaneous needle-mediated interventions are widely used for diagnosing a large variety of diseases where biopsies of tissue are taken for tissue examination. In oncology, for example, biopsies of a pathological tissue region of interest are taken in order to examine whether this tissue is cancerous or not and, in case of a localized tumor, to determine whether the tumor is benign or malignant. A typical application scenario is mammographic visualization of cancerous tumors within a female patient's breast. In order to accurately diagnose and effectively treat the cancer, it may be necessary for a surgeon to excise a portion of the diseased tissue for microscopic examination and histological analysis. To make these interventions more reliable, representative feedback information indicative of the respective kind of tissue in front of the needle is required.

Traditionally, non-palpable breast lesions are excised with a wire as a guiding tool, which greatly facilitates image-guided needle biopsy and surgical resection by providing radiologists with a long wire marker having a small hook portion or spur at one end to be placed into the tissue under radiological control. Radiologic imaging techniques make it possible to display a localized focus of cancerous tissue deep within the internal organs of a patient. Imaging modalities such as X-ray, CT (computed tomography), PET-CT (positron emission tomography/computed tomography), MR (magnet resonance) and US (ultrasound) systems are used in the diagnostics of the diseases and for definition of the needle trajectory as well as for image-guided needle tracking.

Presuming that the guide wire has been accurately positioned, an image-guided needle biopsy based on X-ray, MRI, CT, sonography or hybrid radiography/MR imaging can be performed rapidly and accurately. Once the wire has been inserted into a tissue region of interest, an X-ray image may be taken to document the exact relationship of a wire's hook portion to the target lesion. The wire length thereby serves as a marker and guides the surgeon to a suspected lesion or node.

In general, each medical application requires a specific type of needle. Conventional biopsy needles as known from the prior art differ per clinical application in terms of their shapes, lengths and widths. For example, a biopsy needle used for carrying out soft tissue core biopsies in the neck, the head, the breast, the prostate, and the liver of a patient usually differs from brain biopsy needles, neuro puncture needles, epidural needles, fine aspiration needles for taking biopts from a soft tissue and needle electrodes for radiofrequency ablation of cancerous tissue in terms of its outer diameter and in terms of the length up to which the respective needle is inserted into a respective tissue region of interest. Conventionally, it is thus required to use an X-ray, CT, MR or ultrasound imaging modality for the determination of the lesion location, size, the patient's anatomy to be penetrated as well as for the definition of the needle type to be used.

Nowadays, so called photonic needles are increasingly used. A photonic needle is typically equipped with a light-guiding optical fiber integrated into a hollow cylindrical shaft in the interior of said needle for transferring light from a proximal end on which a generated light beam is incident to a distal end placed in a tissue region of interest around the tip of said needle in the interior of a patient's body, thereby providing an output light, assignable to the intensity of the generated light beam, which is needed for an excitation of a tissue sample to be minimally invasively examined, and transferring a collected beam of the reflected light from the tissue region of interest at the distal end to the proximal end of the needle.

Such a photonic needle may typically comprise a liquid-guiding cannula with a substantially tubular wall and an internal lumen having an open distal end similar to the cannula of a hypodermal syringe for providing a liquid given by a targeted contrast agent or dye fluorescent in the visible spectrum of light to the tip of the needle and applying this liquid to the pathological tissue region of interest so as to mark cancerous tissue anomalies.

In case of photonic needles, the type of tissue to be examined in front of the needle is identified by making use of spectroscopic measurements. To this end, a processing system used for interpreting these measurements is programmed for executing an algorithm which estimates different optical properties, such as e.g. the scattering coefficient and the absorption coefficient of different tissue chromophores (e.g. hemoglobin, oxygenated hemoglobin, water, fat, melanin, etc.).

SUMMARY OF THE INVENTION

Similar to the common biopsy needles as described above, different types of photonic needles with different outer diameters and lengths have to be distinguished, which is because the requirements for tissue classification based on the optical data supplied by a photonic needle strongly depend on the number of different tissues to be traversed. The greater the number of different tissue types and the more similar these different tissue types, the lower is the tissue recognition rate. Furthermore, the algorithm used for analyzing the wavelength spectrum of a certain anatomy region of interest strongly depends on the respective application scenario.

In view thereof, it is the object of the invention to provide a more accurate optical tissue characterization.

This is achieved by the subject matter of the respective independent claims. Further exemplary embodiments are described in the corresponding dependent claims.

The more accurate optical tissue characterization is substantially realized by having a soft tissue differentiation sorted out prior to the biopsy procedure so as to enhance the recognition rate of the applied tissue classification algorithm. Although it is possible to extract the spectral contributions of several types of tissue from a measured wavelength spectrum, the tissue recognition accuracy of tissue classification algorithms might not be good enough, especially if the number of different types of tissues to classify is very large or one tissue compound is predominantly present.

Therefore, a system including a console for processing optical data supplied by a needle device is proposed which allows to recognize the type of the needle device that is being used and to load a software program which is required for the tissue analysis into a system processor.

In general, a system for tissue inspection and for use in different interventions, according to the invention, comprises a needle device including an authentication means corresponding to the type of the needle device, and a console including a plurality of algorithms for processing data from the needle device, wherein the needle device is connected with the console, and wherein an algorithm is selectable depending on the intervention.

The system may further comprise an imaging modality like an X-ray device, a computer tomography device, a magnet resonance tomography device, and an ultrasound device, wherein the imaging modality may be connected with the console and wherein the console may be adapted to process data from the imaging modality, wherein said data may concern to a specific intervention.

The "tissue" investigated by the system may comprise all kind of living or dead tissue, e.g. human tissue, particularly epithelium-tissue (e.g. surface of the skin and inner lining of digestive tract), connective tissue (e.g. blood, bone tissue), muscle tissue and nervous tissue (e.g. brain, spinal cord and peripheral nervous system). "Tissue" may further comprise food products, biomaterials, synthetic materials, fluid or viscous substances, etc.

As another aspect, a needle device according to the invention substantially includes an authentication means identifying the type of the needle device, wherein the authentication means may be electronically readable. An electronically readable authentication means may be provided for example by way of a chip or the like on which identification data are stored, or just by a resistor have a resistance coding the type of the needle device.

On the other hand, the authentication means may also be realized by a characteristic topographical surface (for example like a 3D bar code), which may be located at the connecting site of the needle device, such that the identification of the type of the needle device will be provided at the moment of the coupling between the console and the needle device.

Furthermore, the authentication means may be optically readable like a number, a bar code, a pattern or a color or a combination thereof.

The needle device may further comprise an optical fiber for providing optical data corresponding to the tissue adjacent a distal end of the optical fiber, wherein the distal end of the optical fiber is located at a distal tip of the needle device.

It is noted that the needle device might be, on the one hand, a biopsy needle, a cannula, or a trocar or, on the other hand, might be a catheter adapted to receive a needle by which for example a biopsy will be actually performed.

As a further aspect, a console according to the invention, for use with a needle device providing optical data, and for use in different interventions, generally includes a plurality of algorithms for processing data receivable from the needle device, wherein the plurality of algorithms include a tissue analysis and classification algorithm for each of the different intervention.

The console may be adapted to electronically, mechanically or optically read an authentication means of the needle device representing the type of the needle device used in one of the different interventions, when the needle device is connected with the console, wherein one of the plurality of algorithms is selectable depending on the type of the needle device.

Alternatively, the console may be adapted to receive data from an imaging modality representing one of the different interventions, when the imaging modality is connected to the console, wherein one of the plurality of algorithms is selectable depending on the received information. Therefore, the console may comprise an interface for being connected to an imaging modality used for non-invasive acquisition of image data of a region of interest.

For example, if the console receives data from an imaging modality representing a region of interest of a patient's body, it may be advantageous to have an algorithm which is specialized for the analysis and classification of the kind of tissue which can be expected in said region of interest. Concrete, in case that the region of interest is a head of a patient, an algorithm may be selected which is specialized on analyzing and classifying brain tissue or blood vessels occurring in a head. Depending on said selection, it may be subsequently possible to provide a physician with information about needle devices which may be appropriate for an intervention in said region.

The console may further comprise means for entering a code of the needle device provided by the authentication means and representing the type of the needle device. Here, the code may be manually entered into the console instead of the possibility to automatically sense the code of the needle device, as mentioned above. Therefore, one of the plurality of algorithms may be manually selected for an intended intervention, for example by means of a keyboard, touch screen or mouse.

The plurality of algorithms in the console includes a tissue analysis and classification algorithm for analyzing and classifying the surrounding tissue at a distal tip of the needle device, wherein the tissue analysis and classification algorithm may include a spectral tissue analysis which may be based on an estimation of different optical properties including the scattering coefficient of an emitted light beam originating from the needle device which may be reflected at the surrounding tissue at a distal tip of the needle device and the absorption coefficient of different tissue chromophores including hemoglobin, oxygenated hemoglobin, water, fat and melanin.

The console may thus be adapted to provide information from one of the group consisting of reflectance spectroscopy, fluorescence spectroscopy, autofluorescence spectroscopy, differential path length spectroscopy, Raman spectroscopy, optical coherence tomography, light scattering spectroscopy, and multi-photon fluorescence spectroscopy.

Especially transitions between different tissues may be reliably detected by means of such algorithm. For example, a blood vessel can be detected, even if the X-ray overview-image does not clearly show said vessel, before the needle device causes any unintended lesion.

In other words, the console may be configured for spectrally analyzing optical data supplied by a needle device when being introduced into a tissue region of interest in the interior of a patient's body and configured for executing a tissue classification algorithm for classifying the surrounding tissue at a distal tip of the photonic needle.

Said console thereby comprises an interface for being connected to an X-ray, CT, MR or ultrasound imaging modality of an imaging system used for non-invasive acquisition of image data showing said tissue region of interest and a processing unit for guiding the tissue classification algorithm based on features extracted from the image data of the X-ray, CT, MR or ultrasound imaging modality.

Further, it is provided that said console may be adapted to make use of entered, detected or known information on the needle type and/or on the anatomical region shown in the image data of the X-ray, CT, MR or ultrasound imaging modality so as to enhance the guiding procedure and thus to increase the recognition rate of the tissue classification algorithm by making a pre-selection of the recognition results based on this information.

The console as described above may especially be configured for identifying the type of the needle device when being connected to the console and, based thereupon, loading a special tissue analysis and classification software which is specialized in analyzing and classifying tissue structures of a certain anatomy region for examination of which this type of needle is normally applied.

According to another aspect of the invention, a software program generally includes a set of instructions for identifying one of different interventions and a set of instructions for selecting, corresponding to the identified intervention, an algorithm for analyzing and classifying tissue surrounding a distal tip of the needle device. The software program may further comprise a set of instructions for processing data provided by an authentication means representing a type of the needle device, or by an imaging modality. The software program may be stored and executed on a console for use with a needle device providing optical data, and for use in different interventions. Therefore, the invention relates also to a computer program for a processing device, such that a method including identifying and selecting, might be executed on the console.

The computer program is preferably loaded into a working memory of a data processor. The data processor is thus equipped to carry out the method. Further, the invention also covers a computer readable medium, such as a CD-Rom, at which the computer program may be stored. However, the computer program may also be presented over a network like the worldwide web and can be downloaded into the working memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of embodiments to be described hereinafter and are explained with reference to examples of embodiments.

BRIEF DESCRIPTION OF THE DRAWINGS

The invention will be described in more detail hereinafter with reference to examples of embodiments but to which the invention is not limited.

DETAILED DESCRIPTION OF EXEMPLARY EMBODIMENTS

In the following sections, the claimed invention will be explained in more detail with respect to special embodiments referring to the accompanying drawings.

Figure 1A:
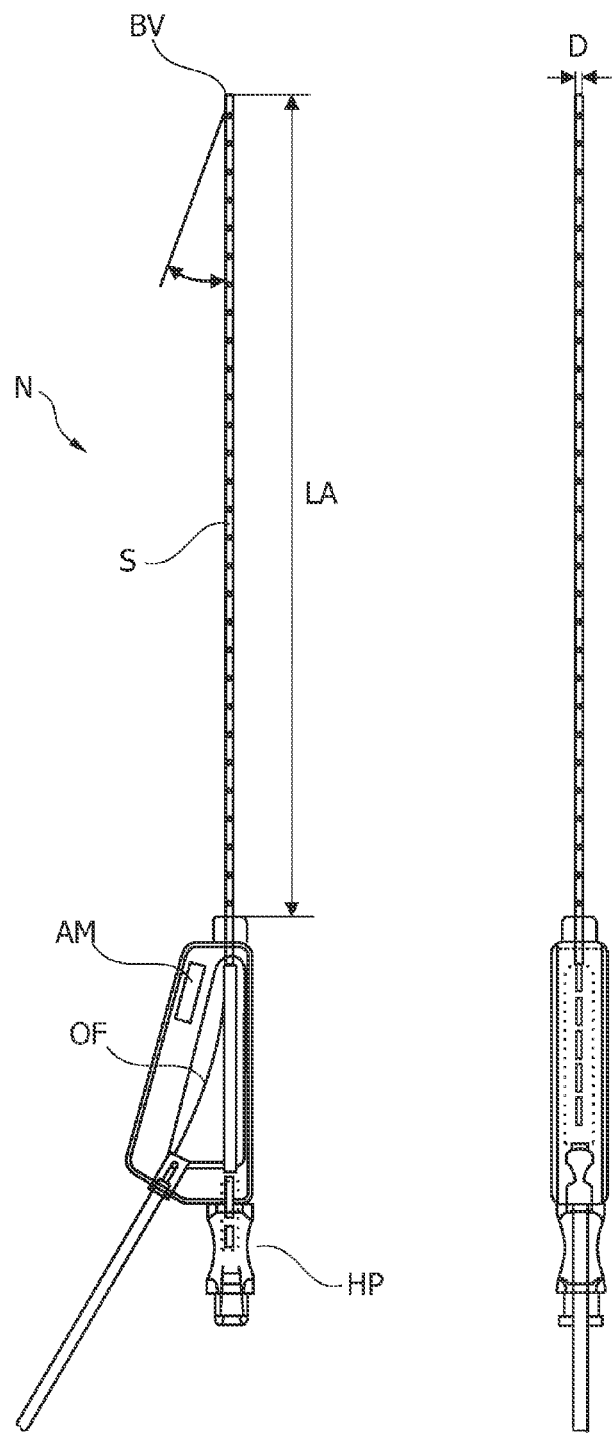
FIG. 1a shows a side view and a top view of a photonic needle.

In FIG. 1a, a side view and a top view of a photonic needle N is shown which can advantageously be applied for minimally invasive tissue inspection by means of optical spectroscopy. As depicted in this figure, such a photonic needle typically comprises a hollow cylindrical shaft S with a bevel BV at its tip portion, a light-guiding means given by an optical fiber OF, integrated into the hollow shaft, and a holder part HP. The optical fiber OF runs from the distal end of the needle, given by the surface of bevel BV, through the interior of the hollow shaft S to the holder part HP and may pass through an opening of the holder part HP out of the needle.

Furthermore, in FIG. 1a is indicated an authentication means AM. It is noted that the authentication means may be electronically, mechanically or optically readable. The authentication means is illustrated in FIG. 1, wherein the position of the authentication means may be on any other location at the needle device including on the outer surface, integrated in the material providing for a part of the needle device like the holder part HP or the shaft S, as well as inside the needle device.

Figure 1B:
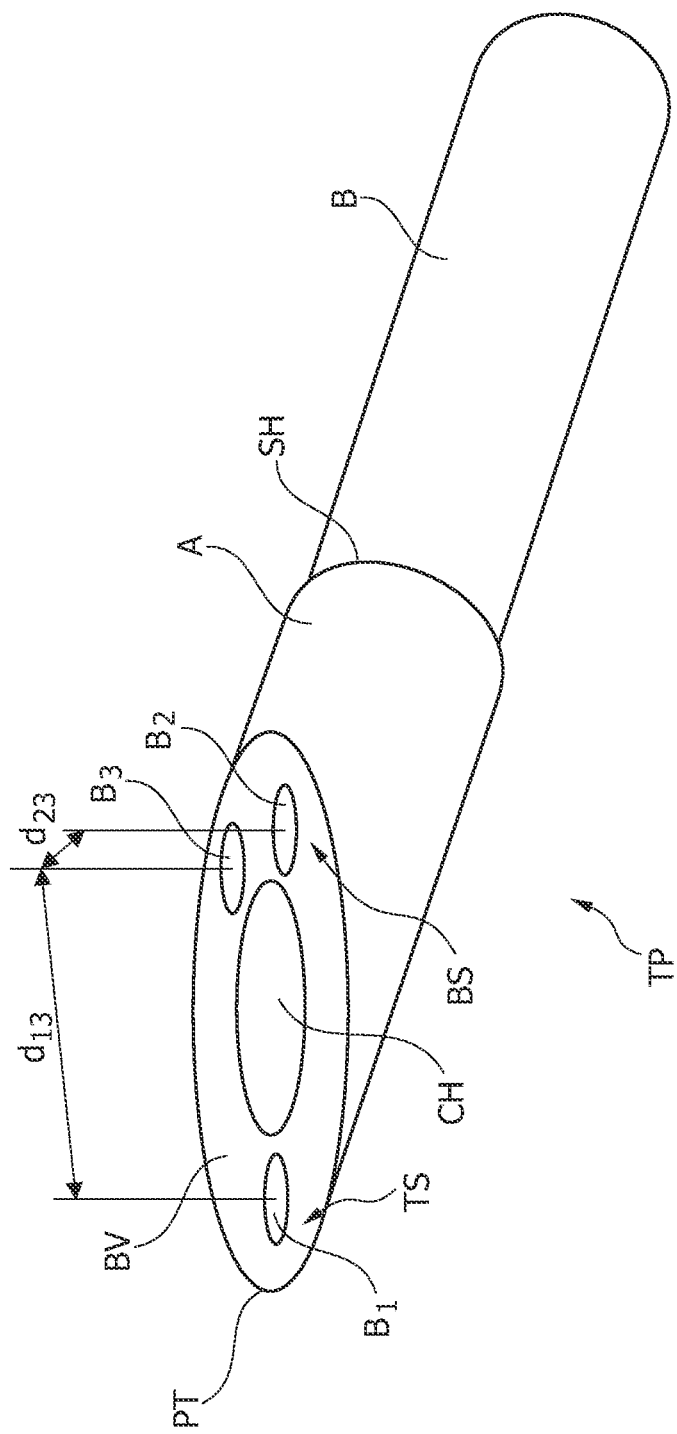
FIG. 1b shows an isometric detailed view of a photonic needle's beveled tip portion.

In FIG. 1b, there is shown an isometric detailed view of an exemplary photonic needle's beveled tip portion TP, which may e.g. be made of an appropriate metal, alloy or ceramic material. The bevel BV forms an acute angle α with the shaft S of the needle N, such that the needle includes a pointed tip PT. As can be taken from FIG. 1b, the tip portion TP may comprise a shaft portion having a thicker section A and a thinner section B such that a step or shoulder SH is formed between these particular shaft sections. The bevel BV comprises a top section TS and a bottom section BS, wherein the top section is a surface area near the pointed tip PT of the tip portion TP.

Parallel to the longitudinal axis LA of the shaft portion, there are provided three small through bores or channels $B_1$, $B_2$ and $B_3$. Each of said small through bores is formed such that an opening of each bore is at the bevel surface BV and the other opening of the bore is in the surface of the shoulder SH, which surface is orientated substantially perpendicular to the longitudinal axis of the shaft portion. The bores $B_1$, $B_2$ and $B_3$ are dimensioned such that an optical fiber might fit into each of them, wherein said fibers might additionally be fixed by gluing. Moreover, said tip portion TP includes a channel CH along the center axis of the shaft portion. Such a channel CH might serve to deliver, for example, contrast agents or drugs to a tissue region of interest or to extract substances from the tissue in which the needle is positioned.

Figure 1C:
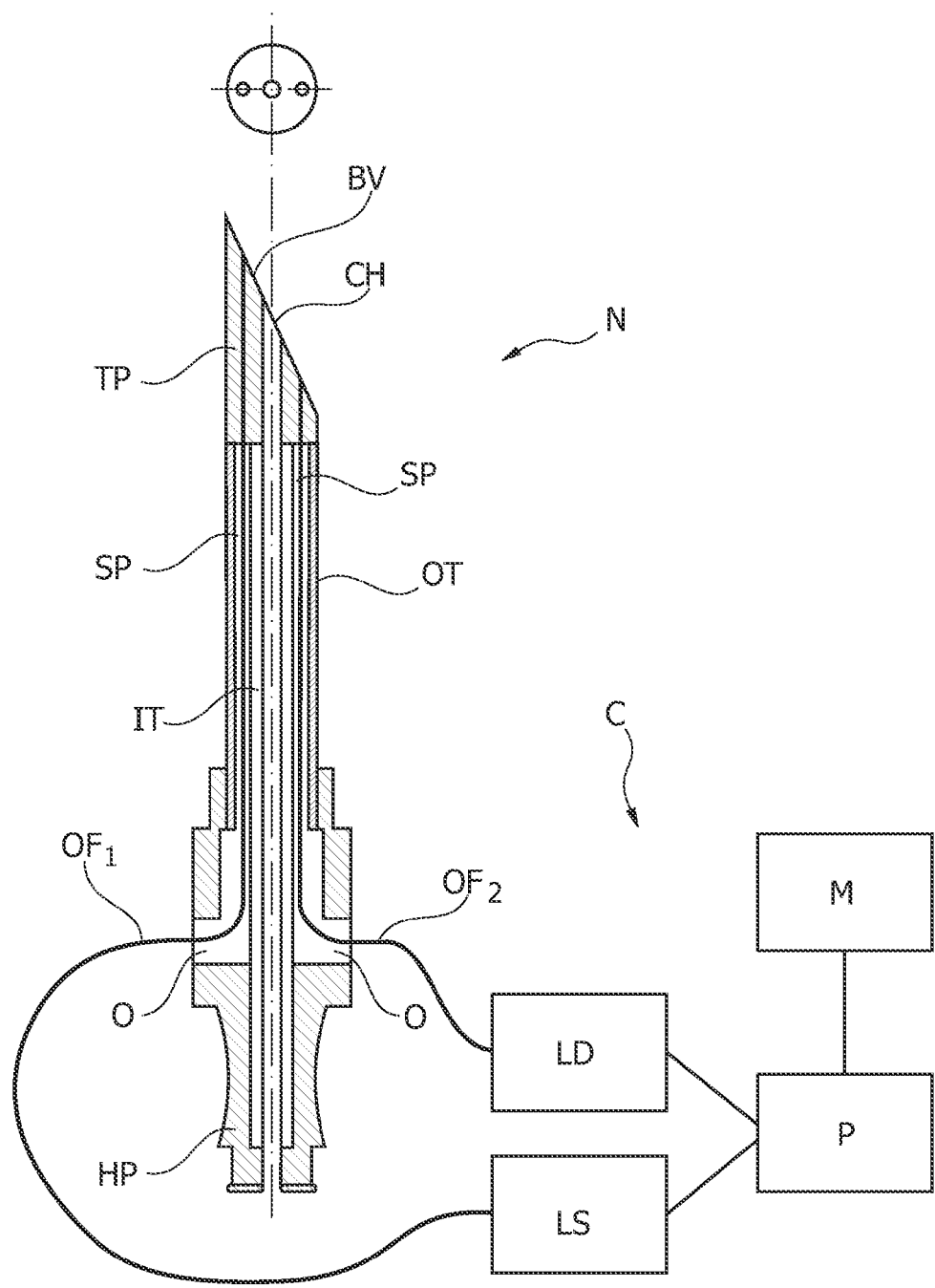
FIG. 1c shows a system including a needle device and components of a console.

FIG. 1c shows a system for processing and displaying a wavelength spectrum of a tissue region of interest which is derived from the collected output light at the proximal end of a light-guiding optical fiber integrated into a photonic needle N. In this illustration, photonic needle N comprises a tip portion TP, an inner tube IT, an outer tube OT and a holder part HP. Two optical fibers, $OF_1$ and $OF_2$, are integrated into a hollow shaft in the interior of the needle.

An important part of the needle is the needle tip (see FIG. 1b), in which e.g. two or three through bores, $B_1$, $B_2$ and $B_3$, may be provided. In each of these bores a fiber is mounted. The tip portion may be fixed to both the inner tube IT and the outer tube OT by welding or gluing, wherein the inner and outer diameters of the inner and the outer tube may be adapted to corresponding diameters of the thicker shaft section A and the thinner shaft section B of the tip portion TP. A hollow space SP between the tubes may be provided into which the through bores in the tip portion are open out. Coming out of the bores in the tip portion, the two optical fibers, $OF_1$ and $OF_2$, are positioned in the hollow space SP between both tubes.

The tip, fibers and both tubes, once assembled, may be fixed to a needle holder HP. Inside the holder the inner tube is connected with a connector to which for instance a syringe or other tubing can be fixed. In this way volumes of fluid can be dispensed through the channel CH of the inner tube IT and tip portion TP without interaction with the optical fibers. The needle holder HP also contains a separate exit O for the fibers. After assembling tip, fibers, tubes and holder, the bevel BV of the needle (i.e. the needle tip) is polished to obtain a proper surface quality for the fibers.

Aside from the system components mentioned above, the console C of this exemplary system comprises a light source LS, a light detector LD, a processing unit μP and a monitor M. The processing unit μP is capable of controlling the light source LS to emit light into the fiber $OF_1$ such that light will be emitted through the distal end surface of the fiber $OF_1$ at the top of the bevel BV into surrounding tissue. Depending on what kind of tissue is in front of the bevel, more or less of the emitted light will be reflected in the direction of the bottom of the bevel to be received by the other fiber $OF_2$. Through the fiber $OF_2$, the light will be led to the light detector LD, which detector is adapted to transform the light into electrical signals. These electrical signals may e.g. be sent by a wire to the processing unit. The processing unit will process the data corresponding to the electrical signals such that the processed data can be visualized on the screen of a monitor M or display. Based on the visualized data, it might be possible to diagnose whether or not a tissue is cancerous and whether a detected tumor is benign or malignant.

Figure 1D:
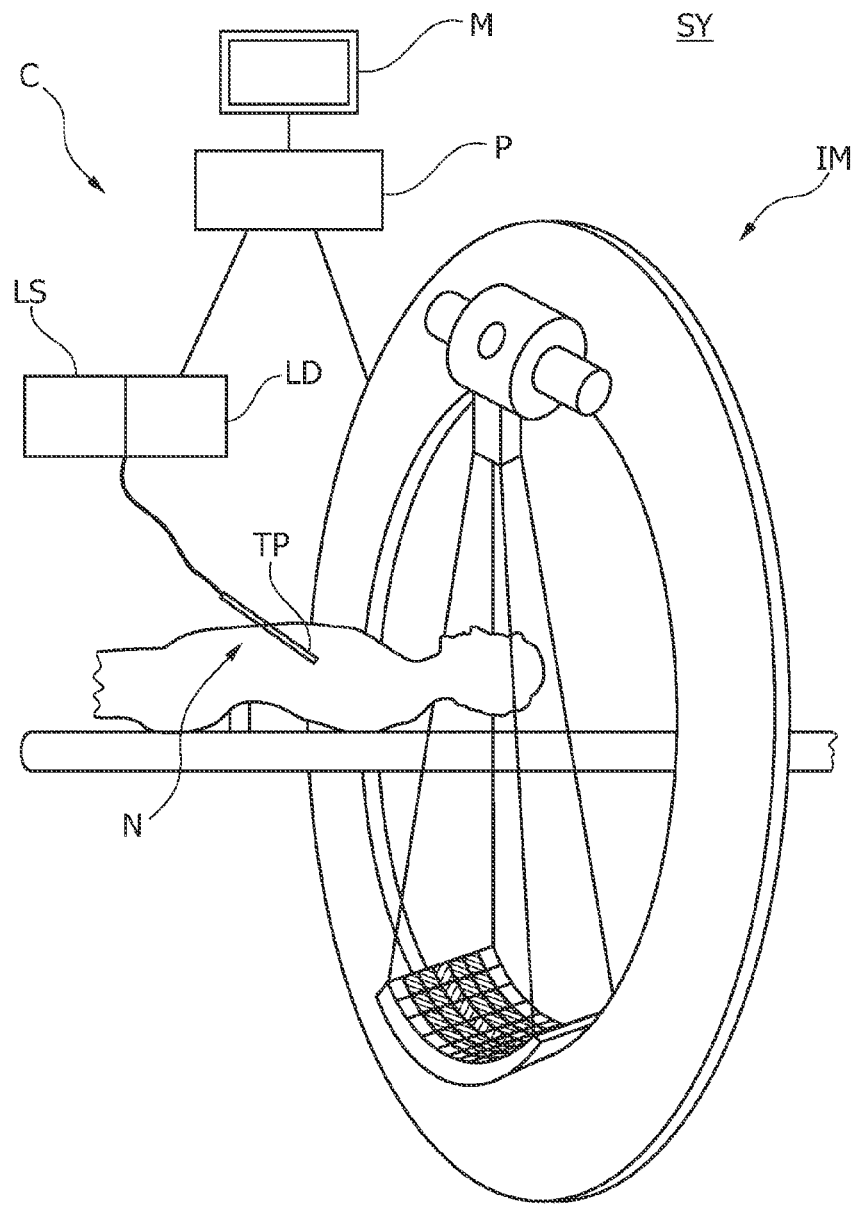
FIG. 1d shows a system according to the invention further including an exemplary imaging modality, FIG. 2 refers to a graphical user interface showing a fluoroscopic image of an application scenario with a needle approaching a patient's spinal column on the right hand side and several icons for activating different applications required for classifying tissue structures in different regions of the patient's body on the left hand side.

FIG. 1d shows an interventional system SY according to an exemplary embodiment of the invention. The system SY comprises an elongated needle device N, a sensor at the tip portion TP of the needle device, an imaging modality IM, and a console C. The exemplary console C includes a light source LS and a spectrograph as a light detector LD. The console further includes a processor unit μP for processing the signals coming from the light detector LD and from the imaging modality IM, and a monitor M for monitoring information for assisting the guidance of the needle device in a body. The imaging device IM includes a radiation source and a detector array.

As illustrated in FIG. 1d, the interventional system SY comprises an image guided X-ray based needle guidance system and a needle device N comprising a sensor, i.e. an optical fiber, which is connected with a console C. The image guided needle navigation system provides integrated 2D/3D imaging and an interactive image guided needle advancement monitoring, all of which is coupled to the optical information obtained by the needle, wherein the X-ray system provides the coarse guidance, while the optical information received from the console, provides the final precise guidance of the tip portion of the needle device.

The exemplary system is able to interactively follow the needle device from the incision to the target point by superimposing 2D fluoro-image on 3D tissue reconstruction and provide molecular tissue information at every point along the needle trajectory that is registered to the position inside the body of the patient. The region along the needle trajectory can be scanned (scan forward and scan aside) in order to provide indications on lesion existence at the molecular level. Preferably in reconstructing what tissue is in front of the needle the X-ray data and the position information of the needle is actively used in the optical reconstruction of what tissue is in front of the needle.

The spectral image data of a tissue region of interest supplied by a photonic needle is fed to a data processing system configured for executing an algorithm which allows to estimate different optical tissue properties, such as e.g. the scattering coefficient and the absorption coefficient of different tissue chromophores (e.g. hemoglobin, oxygenated hemoglobin, water, fat, melanin, etc.) in a tissue region of interest.

Figure 2:
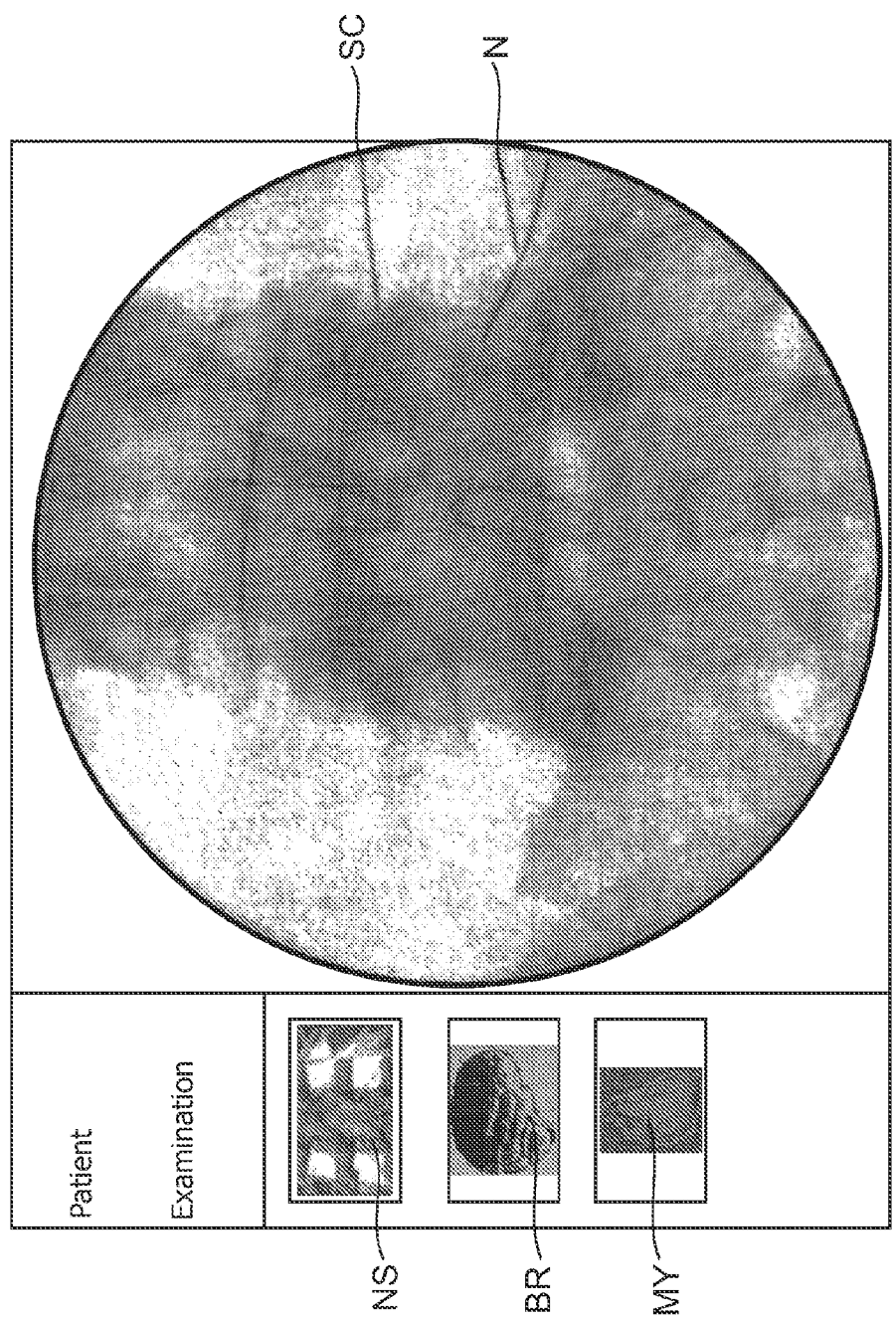

FIG. 2 shows a graphical user interface of an X-ray system as proposed in the scope of the invention. On the right hand side, a fluoroscopic image of an application scenario with a needle N approaching a patient's spinal column SC is shown. On the left hand side, said user interface provides dedicated space for all kind of information regarding the patient. In case the photonic needle is connected to the X-ray system, for example three logos (icons NS, BR and MY) that correspond to a different application will pop up. In this example, the uppermost icon (NS) shows the nervous system in the neighborhood of L4-L5 discs, the mid one (BR) represents the brain, and the lowermost icon (MY) represents the myocardium.

In case the attending physician needs to perform an epidural injection with the photonic needle, then he just needs to click on the uppermost icon NS. Consequently, the software needed to analyze the data will mainly be using the classification algorithm relevant for epidural procedures.

In case the physician clicks on the brain icon BR, the software used for controlling the operation of the photonic needle will load a tissue classification algorithm which is capable of classifying tissue structures relevant for brain procedures. Finally, in case the physician clicks on the myocardium icon MY, the software used for controlling the operation of the photonic needle will load a tissue classification algorithm that estimates the blood concentration (which estimation may preferably be based on the number of hemoglobin and oxygenated hemoglobin chromophores) in order to detect blood vessels and avoid them during the intervention. (In this connection, it should be noted that it is impossible to see blood vessels in fluoroscopy unless a contrast agent is used.)

In accordance with another aspect of the invention, the type of a disposable needle may be identified by reading out the code present by an authentication means at the disposable needle when being connected to the console, in that a physician enters a serial number of the photonic needle into a console which carries out the tissue classification algorithm, or slides the needle along a bar code reader of the imaging system, or in that the physician clicks on any one of said icons so as to indicate the clinical application at hand. If the desired type of X-ray reconstruction algorithm depends on the type of intervention to be executed, it can thus be provided that the X-ray reconstruction method is directly linked to the respective optical reconstruction method.

Figure 3:
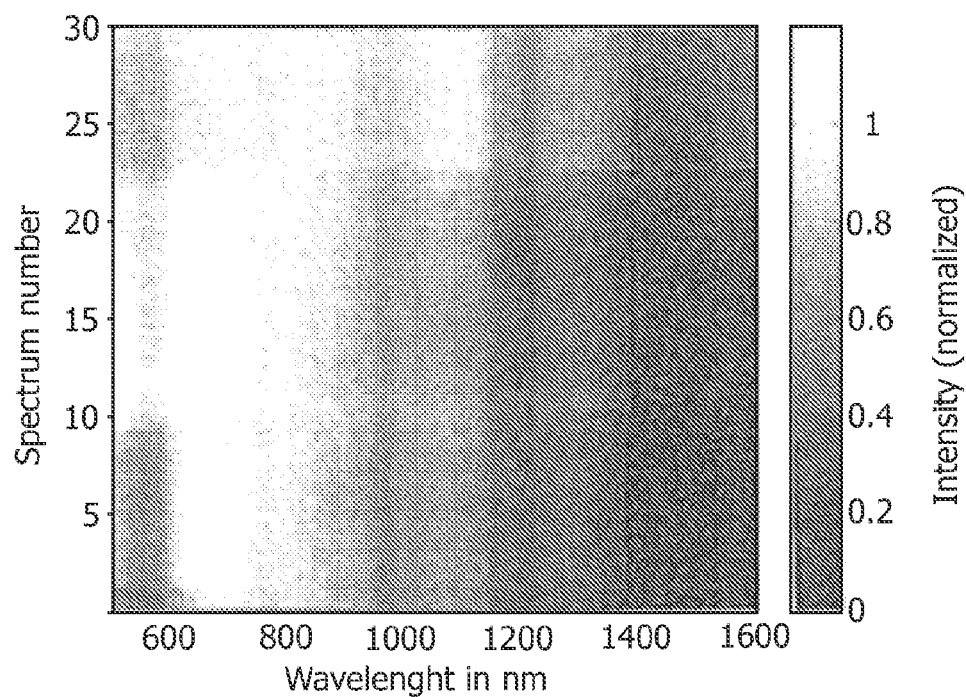
FIG. 3 shows an exemplary gray scale plot of the normalized measured reflectance intensity as a function of wavelength, wherein the respective spectrum number corresponds to the moment at which the particular spectrum was measured during the insertion of the photonic needle into a tissue region of interest, which means that different spectrum numbers correspond to different tissue locations.
Figure 4:
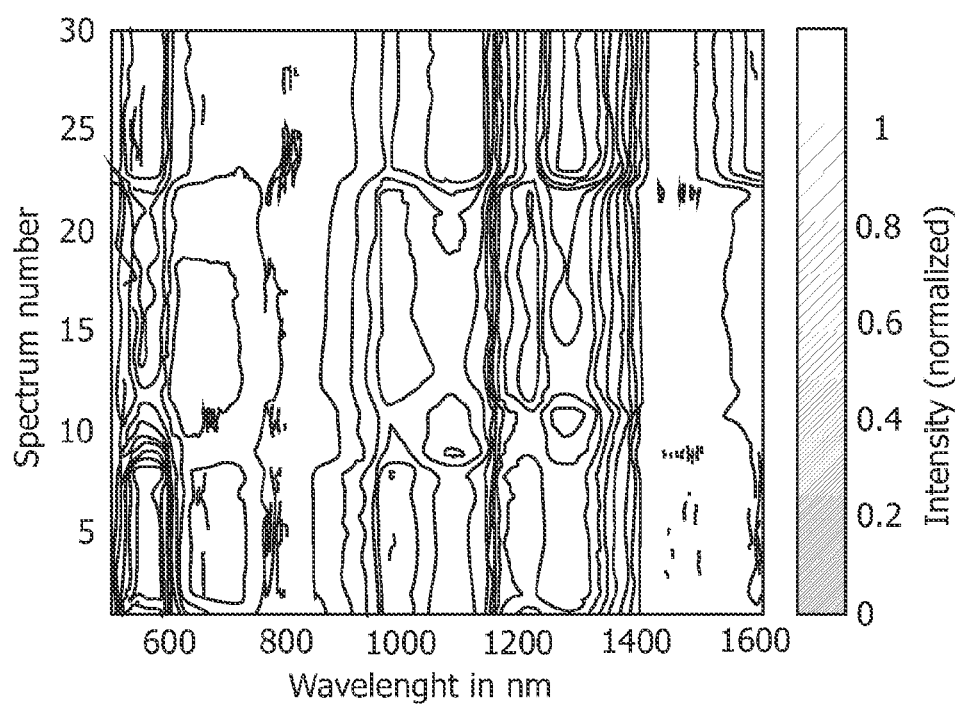
FIG. 4 shows a similar gray scale plot as depicted in FIG. 3, but this time given in the form of a contour plot.
Figure 5A:
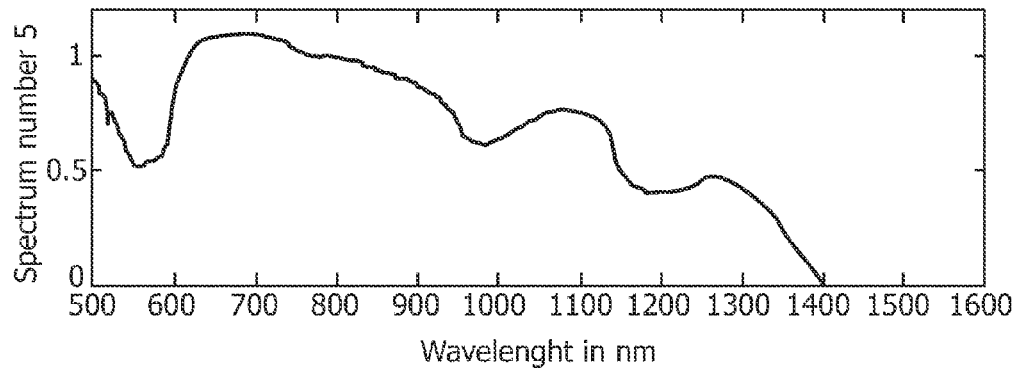
FIGS. 5a-c show characteristics of three exemplary wavelength spectra acquired by means of a photonic needle during an image-guided needle intervention whose spectrum numbers are indicative of different tissue locations within a tissue region of interest.
Figure 5B:
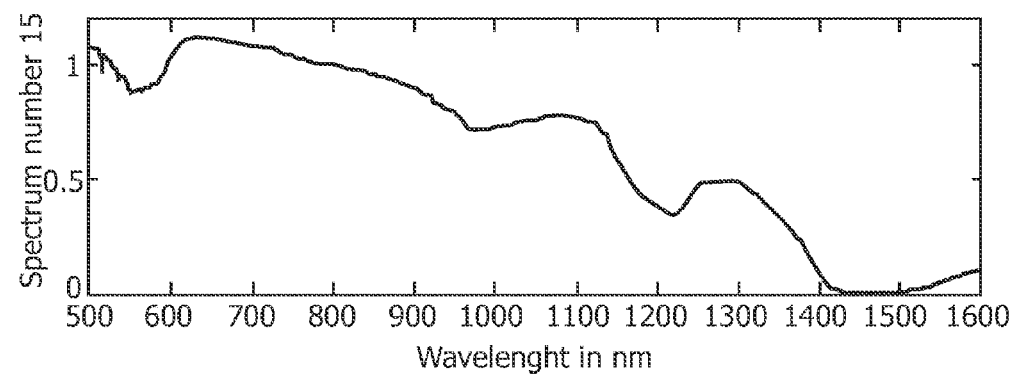
Figure 5C:
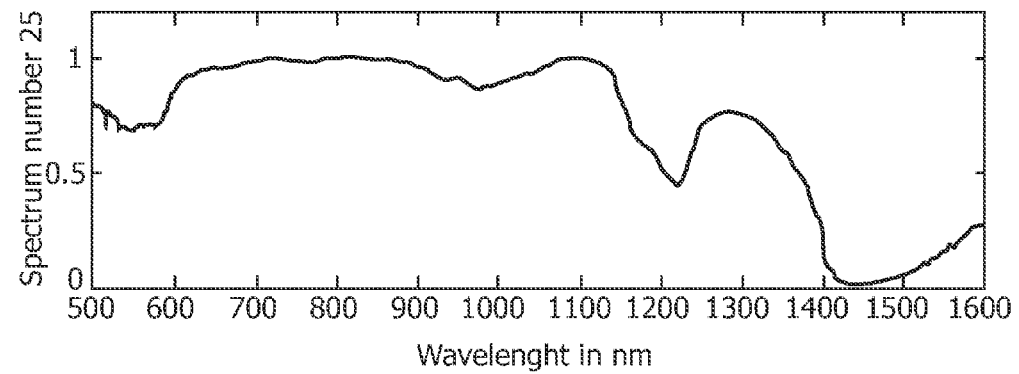

In FIGS. 3 and 4, differences in the normalized reflectance measurements over time can be recognized between different locations within a tissue of interest. In FIGS. 5a-c, characteristics of three exemplary wavelength spectra are shown which have been acquired by means of a photonic needle during an image-guided needle intervention. The spectrum numbers of these spectra are indicative of different tissue locations within a tissue region of interest. The higher the spectrum number, the further the needle has advanced in the tissue.

As can be taken from FIGS. 5a-c, the spectra are sufficiently different for discriminating transitions between different locations within said tissue region of interest when navigating the photonic needle within said tissue. These transitions may not be visible in the X-ray image. However, if we want to go a step further and determine which type of tissue it is, we have to rely on parameters one can extract from the obtained wavelength spectra. These parameters comprise the blood content, the oxygenation of blood, the amount of water present, the fat concentration and the scattering parameter.

It is envisioned that we are able to discriminate a significant amount of tissues based on these parameters. But if we take all the tissues present in a patient's body, it is also possible that some of these tissues are quite similar when relying on the above parameters and that classification may be inaccurate or is no longer possible. It should be noted that other optical methods, such as e.g. diffuse reflectance spectroscopy, differential path length spectroscopy, light scattering spectroscopy, autofluorescence spectroscopy, multi-photon autofluorescence spectroscopy, Raman spectroscopy or optical coherence tomography, can also advantageously be used to discriminate different types of tissue instead of reflectance spectroscopy.

As proposed in the scope of the present application, pre-knowledge is used coming either from the attending physician, from the determined needle type or from another imaging modality such that we know which subset of tissue we will encounter. The tissue classification algorithm can then compare the measured spectra with reference spectra stored in a classification database based on a similarity criterion which is improved by reducing or eliminating classification ambiguities which could possibly arise during the classification procedure.

Photonic needles used in the scope of the present invention can be applied in minimally invasive percutaneous needle interventions, such as e.g. low back pain interventions, in oncology when taking biopsies for diagnosis of cancerous tissue regions or in cases where a tissue characterization around the tip portion of the needle is required. In order to limit the classification database for the translation of an acquired wavelength spectrum to physiological parameters, every needle that is used for intervention is supposed to have a serial number that will inform the embedded software in which type of medical application the respective needle is provided to be used.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE SIGNS

A thicker shaft section of the tip portion
AM authentication means
α acute angle
B thinner shaft section of the tip portion
$B_1$, $B_2$, $B_3$ through bores
BR con representing a patient's brain
BS bottom of the bevel
BV bevel
C console
CH channel
D diameter of the needle shaft
$d_{13}$ distance between bores $B_1$ and $B_3$
$d_{23}$ distance between bores $B_2$ and $B_3$
HP holder part
IM imaging modality
IT inner tube
LA longitudinal axis of the needle
LD light detector
LS light source
M monitor
MY icon representing a patient's myocardium
μP processing unit (microprocessor)
N needle
NS icon representing a patient's nervous system
O opening
OF optical fiber
$OF_1$ first optical fiber
$OF_2$ second optical fiber
OT outer tube
PT pointed tip
S needle shaft
SC a patient's spinal column
SH step or shoulder
SP space between inner and outer tubes
SY system for tissue inspection
TP tip portion
TS top of the bevel

The invention claimed is:
1. A system for tissue inspection and for use in different interventions, the system comprising:
a console including a plurality of tissue analysis and classification algorithms for processing data from different types needle devices for use in the different interventions,
wherein each needle device is a distinct type for use in a distinct intervention; and a needle device of a specific needle type for use in a specific intervention,
wherein the console is operatively connected to the needle device to execute one of the plurality of tissue analysis and classification algorithms depending on the specific intervention.

2. The system of claim 1, further comprising:
an imaging modality out of the group consisting of an X-ray device, a computer tomography device, a magnet resonance tomography device, and an ultrasound device,
wherein the console is operatively connected to the imaging module to select one of the plurality of tissue analysis and classification algorithms depending on data from the imagine modality corresponding to the specific intervention.

3. The system of claim 1, wherein the console is further operable to electronically, mechanically or optically authenticate the needle device for identifying the specific needle type of the needle device.

4. The system of claim 3, wherein the console is further operable to select one of the plurality of tissue analysis and classification algorithms depending on an authentication of the needle service.

5. The system of claim 1,
wherein the needle device includes an optical fiber for providing optical data corresponding to tissue adjacent a distal end of the optical fiber, and
wherein the distal end of the optical fiber is located at a distal tip of the needle device.

6. A console for use with different types of needle devices providing optical data and for use in different interventions, the console including a plurality of algorithms for processing data receivable from the needle devices,
wherein the plurality of algorithms include a different tissue analysis and classification algorithm for each type of needle device, and
wherein the console is operable to execute one of the plurality of tissue analysis and classification algorithms depending on a specific needle type connected to the console for use in a specific intervention.

7. The console of claim 6,
wherein the console is further operable to electronically, mechanically or optically authenticate a type of needle device connected to the console, wherein one of the plurality of tissue analysis and classification algorithms is selectable by the console depending on an authentication of the type of the needle device.

8. The console of claim 6, wherein the console is further operable to receive data from an imaging modality representing one of the different interventions, when the imaging modality is connected with the console, wherein one of the plurality of tissue analysis and classification algorithms is selectable depending on the received data.

9. The console of claim 6, wherein the console further comprises means for manually selecting one of the plurality of tissue analysis and classification algorithms for one of the different intervention.

10. The console of claim 6, wherein an executed tissue analysis and classification algorithm includes a spectral tissue analysis and a classification of the surrounding tissue at a distal tip of the needle device, which is based on an estimation of different optical properties including the scattering coefficient of an emitted light beam originating from the needle device which is reflected at surrounding tissue at a distal tip of the needle device and the absorption coefficient of different tissue chromophores including hemoglobin, oxygenated hemoglobin, water, fat and melanin.

11. The console of claim 6, wherein the console is further operable to provide information from one of the group consisting of reflectance spectroscopy, fluorescence spectroscopy, autofluorescence spectroscopy, differential path length spectroscopy, Raman spectroscopy, optical coherence tomography, light scattering spectroscopy, and multi-photon fluorescence spectroscopy.

12. The console of claim 6, wherein the console further comprises an interface for being connected to an imaging modality used for non-invasive acquisition of image data of a region of interest.

13. A software program encoded in a non-transitory computer-readable medium of a console for use with different needle devices providing optical data and for use in different interventions, the software program causes the console: to identify one of the different interventions, and to select an algorithm for analyzing and classifying tissue surrounding a distal tip of the needle device, corresponding to the identified intervention.

14. The software program of claim 13, wherein the identification of one of the different interventions is based on a code representing a type of the needle device.

15. The software program of claim 13, wherein the identification of one of the different interventions is based on data provided by an imaging modality.

* * * * *